United States Patent

Whitmore, III et al.

[11] Patent Number: 5,961,527
[45] Date of Patent: Oct. 5, 1999

[54] OMNI-DIRECTIONAL PRECISION INSTRUMENT PLATFORM

[75] Inventors: Willet F. Whitmore, III; Winston E. Barzell; Roger Wilson, all of Sarasota, Fla.

[73] Assignee: Barzell Whitmore Maroon Bells, Inc., Sarasota, Fla.

[21] Appl. No.: 08/955,321

[22] Filed: Oct. 21, 1997

Related U.S. Application Data

[63] Continuation-in-part of application No. 08/787,155, Jan. 22, 1997.

[51] Int. Cl.$^6$ .................................................... A61B 19/00
[52] U.S. Cl. ................................................................ 606/130
[58] Field of Search ................................ 606/1, 130, 54, 606/58, 61

[56] References Cited

U.S. PATENT DOCUMENTS

| | | |
|---|---|---|
| D. 271,136 | 10/1983 | Bollinger et al. . |
| 4,543,649 | 9/1985 | Head et al. . |
| 4,694,230 | 9/1987 | Slocum et al. ........................ 901/22 X |
| 5,184,601 | 2/1993 | Putman .................................. 600/102 |
| 5,695,500 | 12/1997 | Taylor et al. ............................. 62/130 |
| 5,695,501 | 12/1997 | Carol et al. ............................. 606/130 |
| 5,697,939 | 12/1997 | Kubota et al. .......................... 606/130 |

OTHER PUBLICATIONS

"Martin" Immobilization Device, Catalog #9102–MA. Mick Radio–Nuclear Instruments, Inc., (1996).
Northwest Transperineal Prostrate Implant Stabilization Device, Transperineal Prostate Implant Dosimetry Service (1996).
"Coton" Stabilizing Device, Catalog #8812–C Mick Radio––Nuclear Instruments, Inc. (1996).
Stabilizer, Hutchinson Medical Designs (1996).
"A.2 Fixation Unit UA1116"; Geninfo, 5 pgs., May, 1996.
"Hawk" and "Falcon" Brachytherapy Stabilizers; Wave Form Systems; 2 pgs., 1998.
"ProScan plus"; Brachytherapy Seed Guide and Probe Holder: 3 pgs., 1996.
"Brachytherapy Ultrasound System"; Carolina Medical Inc.; 4 pgs., 1996.

*Primary Examiner*—Michael Buiz
*Assistant Examiner*—Vy Q. Bui
*Attorney, Agent, or Firm*—Pennie & Edmonds LLP

[57] ABSTRACT

An apparatus for supporting and facilitating accurate positioning, both linearly and angularly of a medical device such as an ultrasound probe, a medical instrument or an imaging device. The apparatus is capable of both gross and precise omni-directional movements with the medical device attached, while remaining connected to stationary objects such as a portable floor stand and/or operating table. After gross manual placement and approximate positioning, the fine tune mechanism of the attached medical device is locked in positioned and secured to two fixed points. Exact positioning is then achieved by the precision movements which are available in all three linear directions and rotational axes. By this arrangement which allows preattachment of the medical device or instrument (i.e., an ultrasound probe) to the apparatus prior to positioning in the patient, quicker, more accurate and more reproducible medical device positioning and placement are achieved.

16 Claims, 10 Drawing Sheets

OMNI-DIRECTIONAL PRECISION INSTRUMENT PLATFORM

CROSS-REFERENCE TO RELATED APPLICATIONS

This application is a continuation-in-part of copending application Ser. No. 08/787,155 filed Jan. 22, 1997.

TECHNICAL FIELD

This invention relates generally to a support apparatus for precision medical instruments, and more particularly to an adjustable support apparatus and system for ultrasound imaging probes and other instruments for use in surgery.

BACKGROUND ART

As advances are made in the medical field, surgical procedures requiring precise positioning of monitoring and surgical tools become necessary. For example, radiologists perform numerous percutaneous guided biopsies using ultrasound and computer aided tomography ("CAT") scanning techniques, magnetic resonance imaging techniques and fluoroscopic imaging techniques. Biopsies and other percutaneous procedures are performed using a variety of needle-like instruments. It would be advantageous to stabilize such instruments or at least be able to manipulate them in a more precise manner than with manual operation.

For example, one currently widely applied and popular method for the treatment of prostate cancer is the percutaneous transperineal implantation of radioactive seeds of either Iodine-125 or Palladium-103. This procedure is performed with the patient in the lithotomy position, using an ultrasound imaging probe placed in the rectum to monitor seed placement. A template arrangement which is kept in precise linear orientation with the ultrasound probe must be accurately oriented adjacent to the perineum in relation to the prostate, and locked in position throughout the procedure to achieve optimum seed placement. Precise and reproducible orientation of the ultrasound imaging probe in the rectum is the key element in both the calculations required for determining the number and distribution of radioactive seeds required for treatment and their subsequent placement using pre-loaded needles guided by the perineal template and real time ultrasound imaging. This form of treatment for prostate cancer has been increasing in popularity because of minimal patient morbidity compared to other available treatments and the potential for improved efficacy due to increasingly accurate methods of seed placement.

Presently, there are many homemade and commercially available devices for holding, manipulating and stabilizing the various commercially available ultrasound imaging probes designed for use in this procedure. None of these devices have achieved wide acclaim because of significant limitations in their ease of use. In general, these devices suffer from the same basic limitation in that they are "post-insertion" probe fixation devices where the probe is first inserted into the rectum and then affixed to a stand. This inevitably leads to a reorientation of the probe, vis-à-vis the insertion cavity, and valuable time is wasted in recreating mechanically the desired probe orientation that was readily achieved with the freedom of omni-directional manual movement.

In an attempt to remedy these shortcomings, certain "pre-insertion" fixation devices have been developed. In these devices, the probe is first affixed to a stand and then the combination of the fine adjustment mechanism with the probe affixed is released to the free "omni-directional" mode to enhance insertion of the probe into the body of the patient. For prostate cancer treatment, for example, the probe is manually inserted into the rectum and, once the desired orientation is achieved as viewed and confirmed by the monitored ultrasound images, the device is then "set" in the "fixed" mode.

Many currently available devices provide multi-axis movement, but movement in one or more of these axes is clumsy, inaccurate and risks significant loss of orientation in other axes during adjustment, or control of the fine adjustment is severely limited. Moreover, such current devices are cumbersome and tend to either be heavy and/or broad-based to achieve floor stand based stability or spatially cumbersome table-mounted structures which tend to obstruct the surgeon's movements and patient access.

Several presently available examples of post-insertion cumbersome devices for prostate treatment are available in the marketplace. One such device is available from Seed Plan Pro of Seattle, Wash. called the Northwest Transperineal Prostate Implant Stabilization Device. Another such currently marketed device very similar thereto is offered by Hutchinson Medical Designs. A third similar immobilization device offered by Mick Radio-Nuclear Instruments, Inc. of Bronx, N.Y. is called the Cotan Stabilizing Device. Mick also distributes the Martin Immobilization Device which can be used as a "pre-insertion" fixation device but has no fine adjustment mechanism for positioning after insertion. Thus, there remains a need for improved holding, manipulation and stabilizing devices for use in this procedure. In addition, there are numerous other medical procedures where enhanced holding, manipulation and/or stabilizing devices can be helpful.

SUMMARY OF THE INVENTION

The present invention overcomes the above prior art shortcomings and includes the following features:

1. A universal mounting platform on which a variety of commercially available imaging probes, needles or similar instruments may be attached prior to insertion of the instrument into the body of the patient;

2. Six axis, fine adjustment for the mounting platform, which provides positive control of probe movement in the X, Y and Z directions and rotation about the X, Y and Z axes for optimum probe orientation and allows for any probe or instrument to be properly "zeroed" at the desired location for accurate measurement and seeding; or other treatment.

3. A set of lockable two-segment articulating arms having end universal joints allowing for low resistance, free-hand, manual instrument placement while the instrument remains fully engaged to the platform apparatus and floor and/or operating table whereupon the ideal manual placement may be quickly fixed in place and secured to two fixed points;

4. A universal stabilizing arm which adapts to any table without modification and, in combination with the portable floor stand, provides a multi-functional unit which can be used with or without the floor stand or, after initial placement, transferred from the floor stand to full table mounting support without loss of position;

5. A light, freely mobile, wheeled, stable floor stand with adjustable feet and one-step lockdown mechanism; and 6. An offset base of the stand to provide wide-base stability while allowing the operator to stand close thereto without interference.

The present invention has applicability to other surgical procedures which require steady, but mobile instrumentation such as cryosurgery, thermotherapy and laser surgery and any procedure where precision movement of imaging or operating instrumentation is required. In addition to the application with prostate cancer seed implantation described above, this omni-directional precision instrument platform apparatus can be used in minimally invasive surgery for prostate cancer and BPH, including laser ablation of benign prostatic hyperplasia, transurethral needle oblation of the prostate, microwave therapy for both BPH and prostatic carcinoma, and cryosurgery for prostatic carcinoma.

Furthermore, this apparatus is useful in percutaneous surgical biopsies. Radiologists typically perform such procedures utilizing any one of a wide variety of radiological instruments or probes to assist in locating or contacting the organ or tissue to be biopsied. CAT scanning and ultrasound x-ray, fluoroscopic or MRI imaging can be used to perform precision biopsy with the present apparatus. In all these minimally invasive procedures, and in other fields of surgery as well, there is great need and potential for an instrument fixation device which is as versatile and precise as that which is disclosed and claimed herein.

This invention is specifically directed to an apparatus and system for supporting and facilitating accurate manual positioning, both linearly and angularly, of an ultrasound probe needle biopsy guide or other instrument used during surgical or diagnostic procedures and, thereafter for securing that positioning with respect to, and while remaining connected to, a stationary object such as a portable floor stand included in the system and/or an edge of a table and the like. After freehand manual positioning of the imaging device or instrument which has been previously fixed to the fine adjustment mechanism, the combination is "set" and further finely controlled movements and angular reorientation in all three linear directions and rotational axes, respectively, (i.e., omni-directional) may be made by adjusting mechanisms of the apparatus provided. By this arrangement, quicker, more accurate and/or reproducible imaging or instrumentation is achieved.

BRIEF DESCRIPTION OF THE DRAWINGS

FIG. 8 is a side perspective view of the system 150 which includes the apparatus 10 shown in FIG. 3 supported on the portable floor stand 100 of FIG. 7 and articulating lockable arms 120 and 120a.

DETAILED DESCRIPTION OF THE INVENTION

Figure 1:
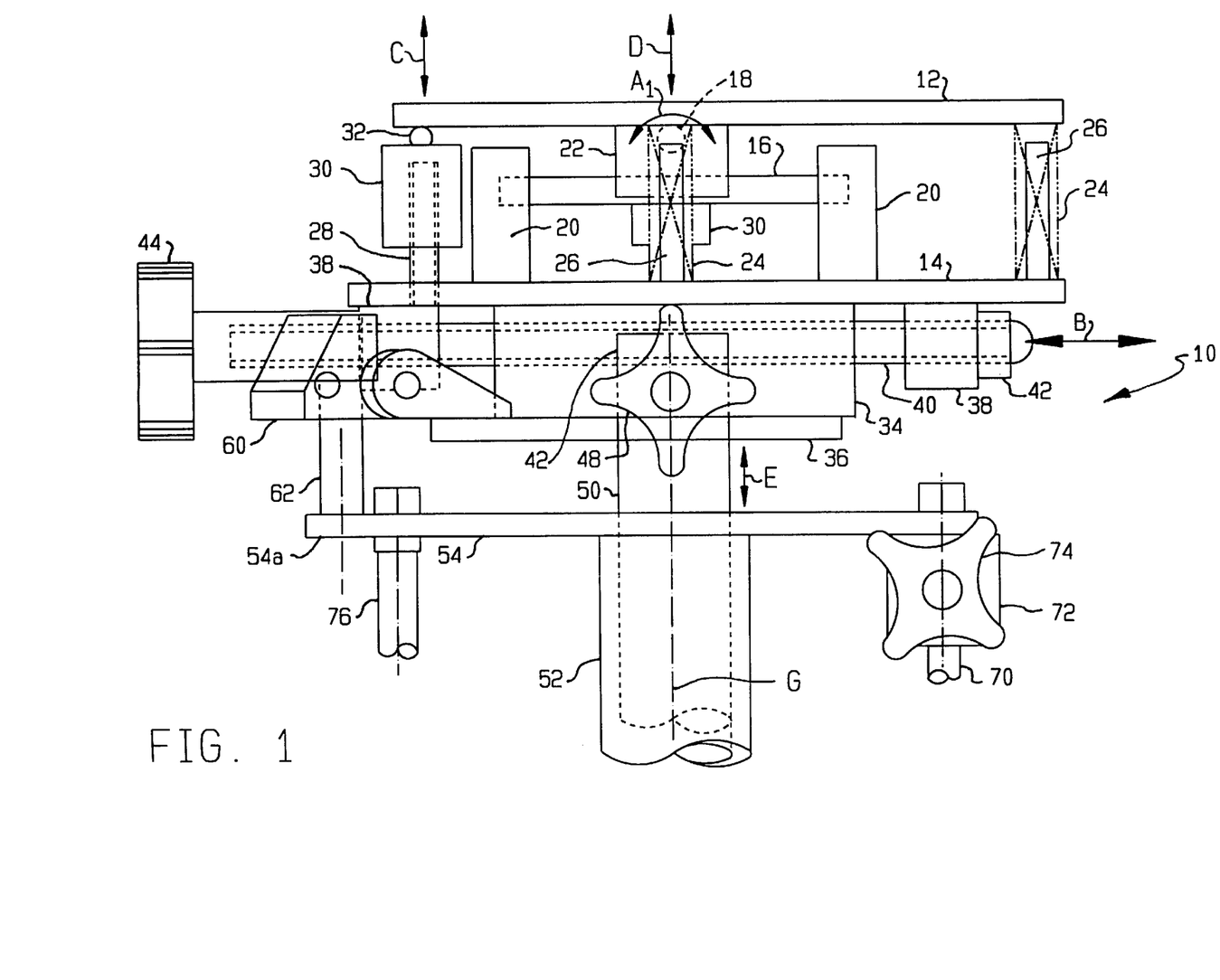
FIG. 1 is a side elevation view of the preferred embodiment of the apparatus 10 with one rotational adjustment knob 68 and associated mechanism removed for clarity.
Figure 2:
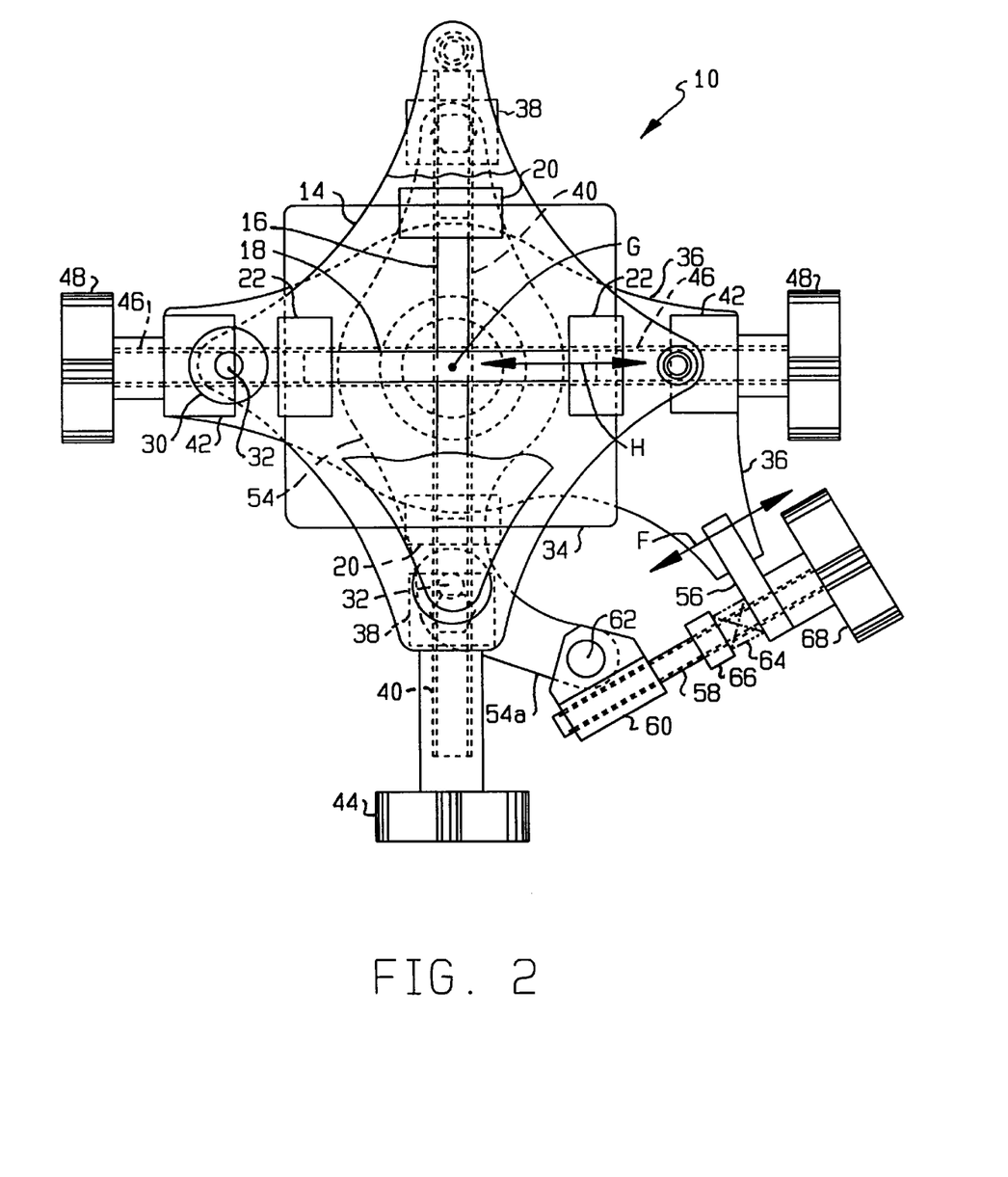
FIG. 2 is a top plan broken view of FIG. 1.

Referring now to the drawings, and particularly to FIGS. 1 and 2, the preferred embodiment of the omni-directional position and orientation adjusting apparatus of the invention is shown generally at numeral 10 for use in placement of seedings for treating prostate cancer.

Figure 3:
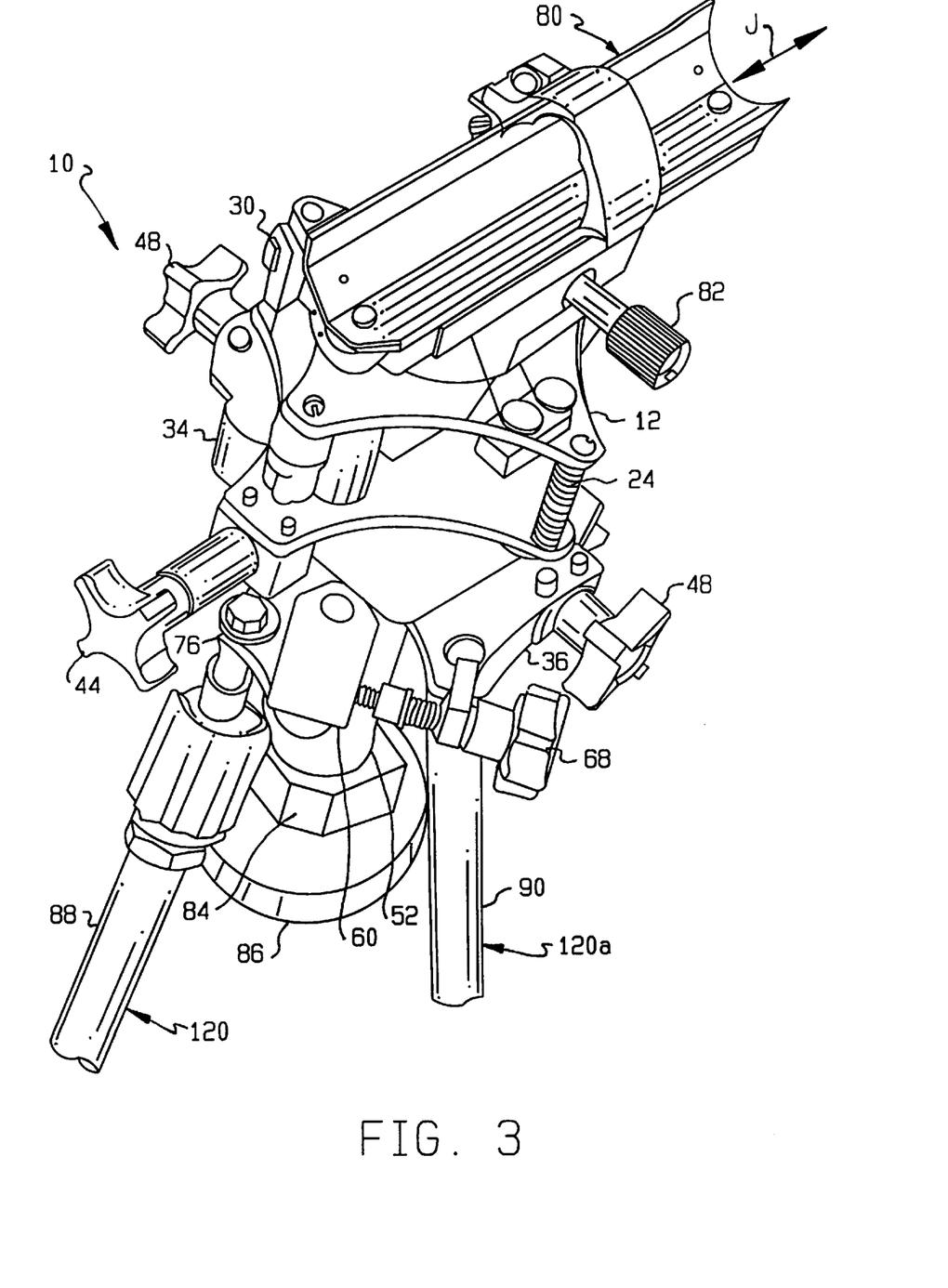
FIG. 3 is a perspective view of the apparatus of FIG. 1 and including a stepping device 80 for receiving a transrectal ultrasound imaging probe (not shown) and upper portions of lockable articulating arms 120 and 120a of the system.

The apparatus 10 includes first, second, third and fourth descendingly spaced and somewhat coextensive plate members 12, 14, 36, and 54. The first or upper plate member 12 is structured as best seen in FIG. 3 for supportive connection with a stepping device 80 (not shown in FIGS. 1 and 2) which is commercially available for receiving a transrectal ultrasound imaging probe and other similar precision medical instrumentation. Generally positioned between the second or intermediate plate 14 and the upper plate 12 is an arrangement which effects rotational positioning about a longitudinal and a transverse axis therebetween. The upper and second plates 12 and 14, respectively, are pivotally connected one to another by universal cross members 16 and 18 which are themselves connected together centrally and connected at each end thereof into support blocks 20 and 22, respectively, blocks 20 being connected atop second plate 14 while blocks 22 are connected to the lower surface of upper plate 12. By this arrangement, upper plate 12 is rotatable about the orthogonal longitudinal and transverse axes of cross members 18 and 16 in the direction of arrows A1 in FIG. 1 and A2 in FIG. 4, respectively.

Two upright compression springs 24 oriented at 90° to one another about upright axis G with respect to the axes of cross members 16 and 18 are positioned between aligned end portions of plates 12 and 14. A guide pin 26 connected to second plate 14 within each spring 24 maintains the stable configuration of each spring 24 under compression. Two adjusting members 30 which are threadably engaged onto threaded shafts 28 mounted and upwardly extending from the opposite ends of second plate 14 from springs 24. A spherical ball 32 positioned between upper plate 12 and the upper end of each adjusting member 30 provides for minimal frictional contact at that point so that, as adjusting members 30 are each rotated about their respective threaded shafts 28, movement in the direction of arrows C and D effects the angular orientation A1 and A2. Instead of the spherical ball, a conical or triangular shaped point can be used to achieve low friction contact with the plate.

A plastic spacer block 34 is positioned between second plate 14 and third plate 36, spacer block 34 being slideably positioned therebetween. Two fully threaded shafts 40 and 46 are threadably engaged in orthogonal fashion through block 34. Threaded shaft 40 slideably engages through end support blocks 38 which are connected near each longitudinal end of second plate 14, while threaded shaft 46 is slideably engaged through end support blocks 42 connected adjacent each lateral end of third plate 36. Adjusting knob 44 at one end of the threaded shaft 40 is provided to effect linear movement of second plate 14 in the direction of arrow B with respect to block 34 and third plate 36. Adjusting knobs 48 at each end of threaded shaft 46 facilitate lateral movement in the direction of arrow H of second plate 14 with respect to block 34 and third plate 36.

Angular orientation about the upright longitudinal axis G of this apparatus 10 is effected by rotation of adjusting knob 68 and threaded shaft 58 (not shown in FIG. 1). Threaded shaft 58 is threadably engaged into plastic block 60 which, in turn, is held for pivotal movement only about pin 62, the lower end of pin 62 being connected to one end 54a of fourth or lower plate 54. Frictional tensioning and positioning of knob 68 against bracket 56 connected to third plate 36 is accomplished by threaded nut 66 against spring 64. By suitable rotation of adjusting knob 68, movement of flange 56 in the direction of arrow P effects rotational movement of third plate 36 and, consequently second plate 14 and upper plate 12, about the vertical axis G.

Figure 4:
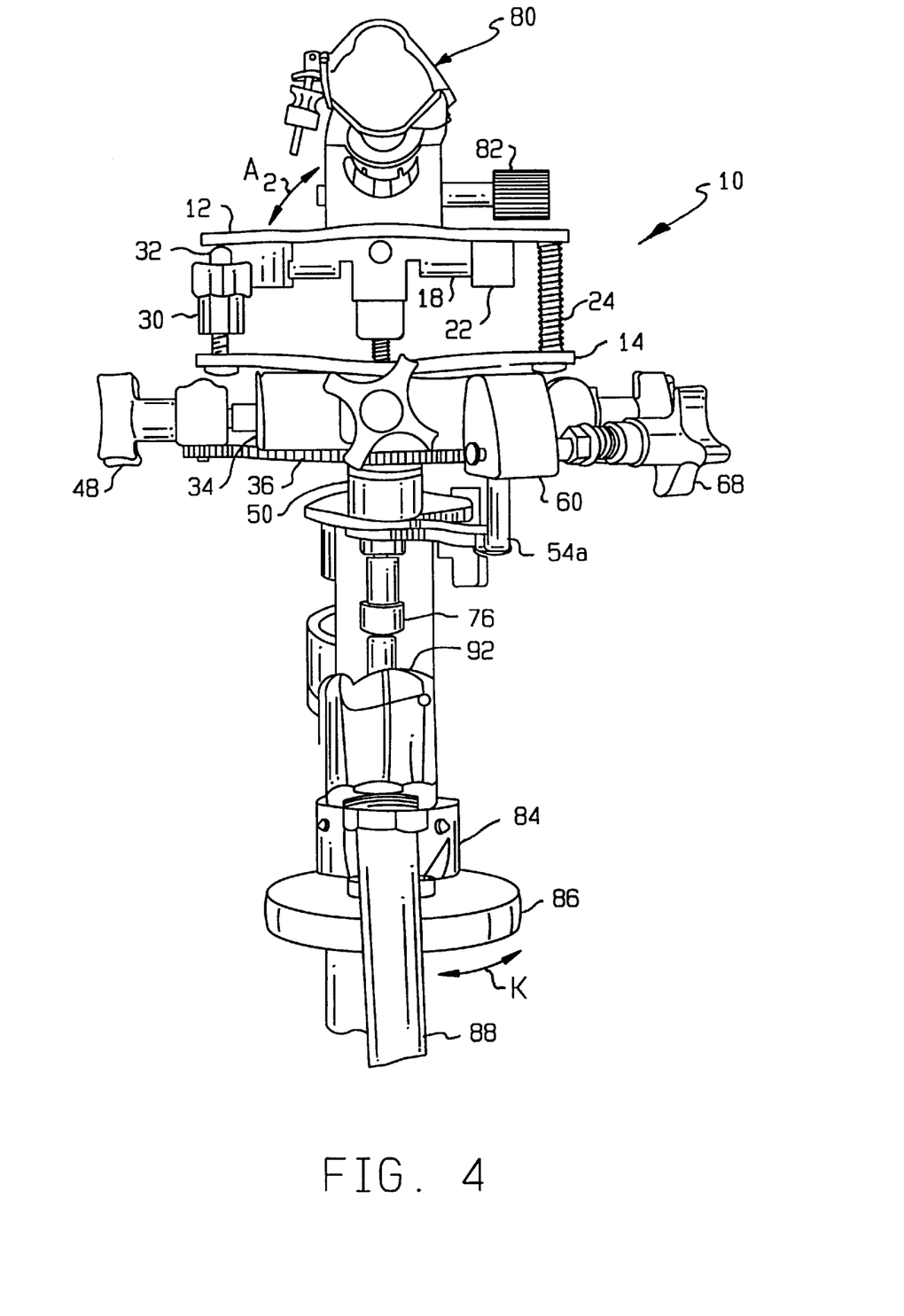
FIG. 4 is a front end elevation view of FIG. 3.
Figure 5:
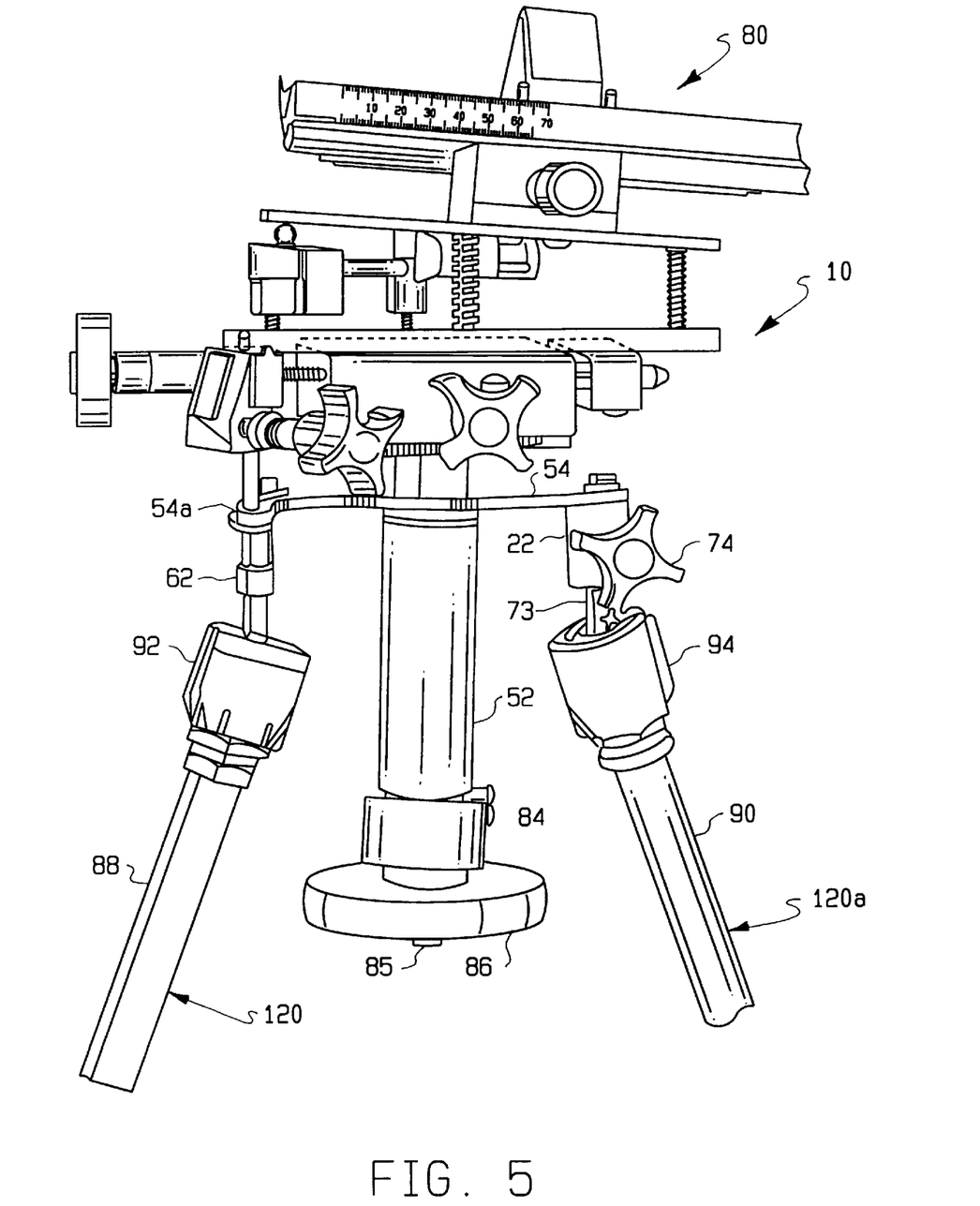
FIG. 5 is a right side elevation view of FIG. 3.

Referring now to FIGS. 3, 4 and 5, the apparatus 10 also includes a support tube 50 which slideably engages within an outer support tube 52 connected and downwardly extending from lower plate 54. By this arrangement, in combination with the structure and function associated with adjusting knob 86 previously described, only vertical movement in the direction of arrow B between third plate 36 and lower plate 54 is provided. To achieve fine vertical adjustment in the direction of arrow E, a threaded shaft 85 seen in FIG. 5 which is connected to, and extends downwardly from support tube 50, threadably engages into plastic adjusting wheel 86. The plastic adjusting wheel 86 is held for rotational movement only with respect to outer support tube 52 by block 84. The vertical movement adjusting wheel 86 and associated cooperating members at the lower end of outer tube 52 of FIG. 1 is best seen in FIG. 3.

Figure 6:
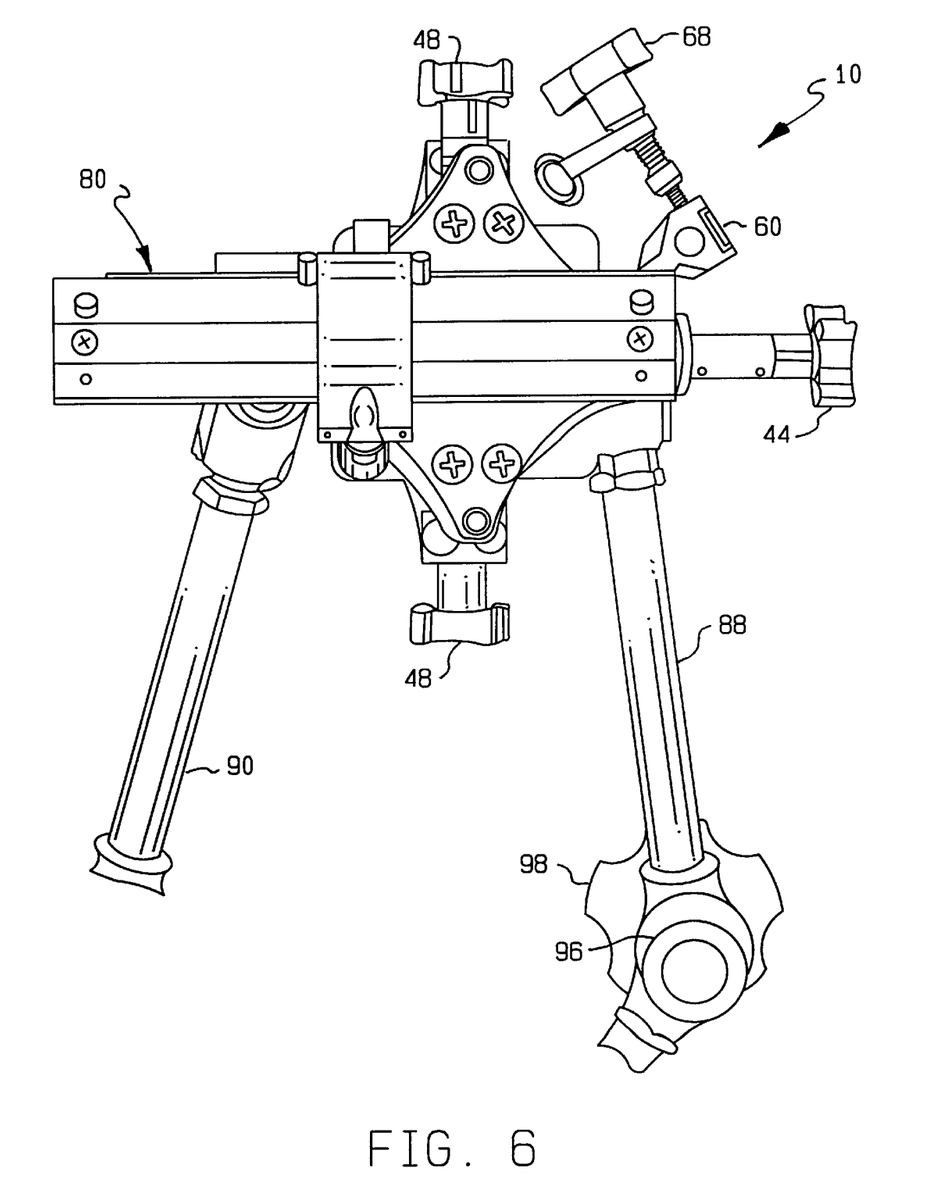
FIG. 6 is a top plan view of FIG. 3.
Figure 7:
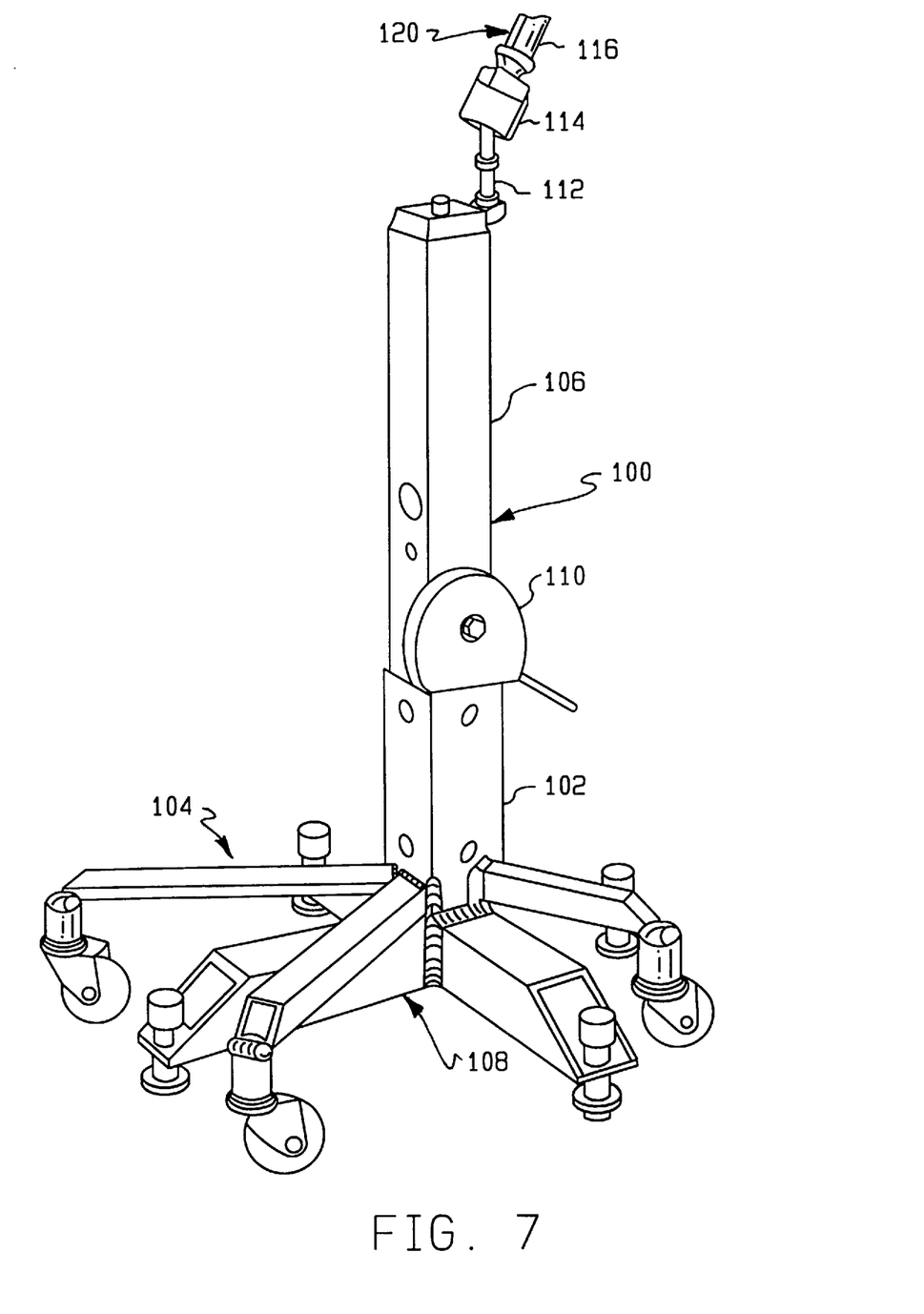
FIG. 7 is a perspective view of a portable floor stand and a lower end of the lockable articulating arm 120 of the system.
Figure 8:
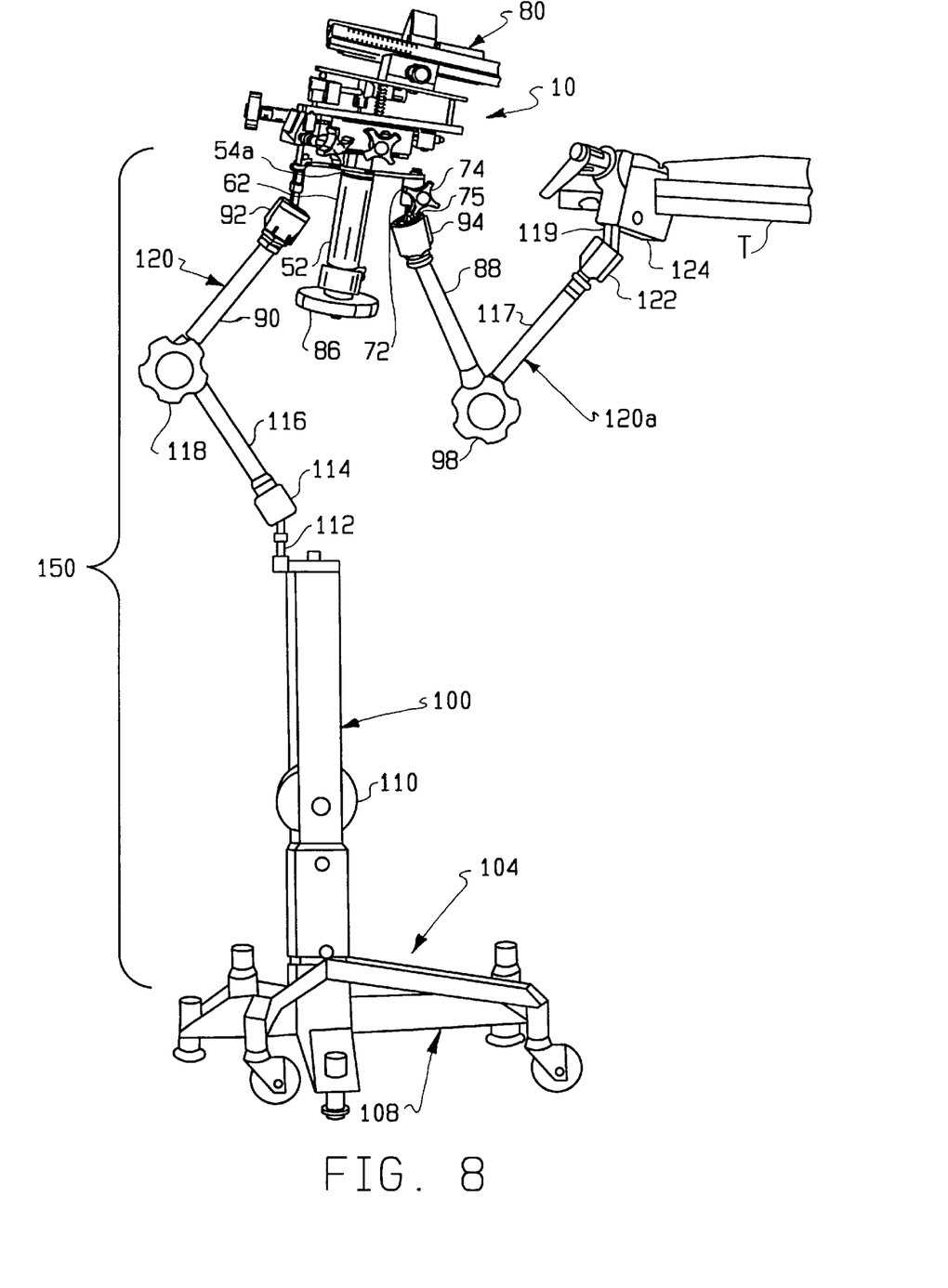

Referring now to FIGS. 6 to 8, the entire system of the present invention is shown generally at numeral 150 and includes the apparatus 10 previously described, articulating lockable arms 120 and 120a and a portable floor stand 100. The floor stand 100 seen best in FIG. 7 is structure to facilitate both easy rolling during transport and quick stationary lockability during use. A rolling frame 104 includes an upright rectangular tubular member 102 and radially extending legs having rolling wheels downwardly disposed at each end. A lockdown frame 108 also includes an upwardly extending rectangular tubular member 106 which slideably engages within tubular member 102. Disposed at the lower end of tubular member 106 is a stabilizing base which includes radially extending arms and non-skid floor contact members. An eccentric adjusting cam 110 is pivotally connected to tubular member 106 such that the periphery of the adjusting member 110 contacts one upper margin of tubular member 102. By rotation of the adjusting member 110, the lockdown member 108 is either placed in contact with the floor or elevated to place the wheels in contact with the floor. By this arrangement, once the entire system 150 is generally positioned as desired, the floor stand 100 may be quickly locked in place to secure that overall positioning.

In this system embodiment 150, two articulating lockable arm members 120 and 120a are provided. Each of these arm members 120 and 120a include two separate arm segments 90/116 and 88/117, respectively which are each pivotally connected one to another at locking knobs 118 and 98, respectively.

Each of the ends 92, 94, 114 and 122 of these articulating arm members 120 and 120a include universally movable support shafts 62, 73, 112 and 119, respectively. The lockable articulating arms 120 and 120a are thus angularly orientable at three locations when locking handles 98 and 118 are released and simultaneously lockable after being selectively positioned. These lockable articulating arms 120 and 120a are commercially available and are called Three-Link locking lever mechanisms. Such devices are included in the prior art Martin Immobilization Device described in the background.

Connected to shaft 119 is a table clamp 124 which is quickly engagable onto an edge of a table T by locking handle 126. While shaft 112 of articulating arm 120 is shown threadably engaged into the upper end of floor stand 100, a similar self-locking member 124 may be substituted therefor as will be described in FIG. 9.

By this arrangement, after floor stand 100 has been generally positioned with respect to a patient or an operating table and locked in that position as previously described, a precision medical instrument such as an ultrasound imaging probe which has been mounted in stepping member 80 may be manually positioned while articulating arm members 120 and 120a are in the unlocked position. Thereafter, by simply rotating locking knobs 98 and 118, the manually selected position and orientation of the precision instrument is fully maintained.

Figure 9:
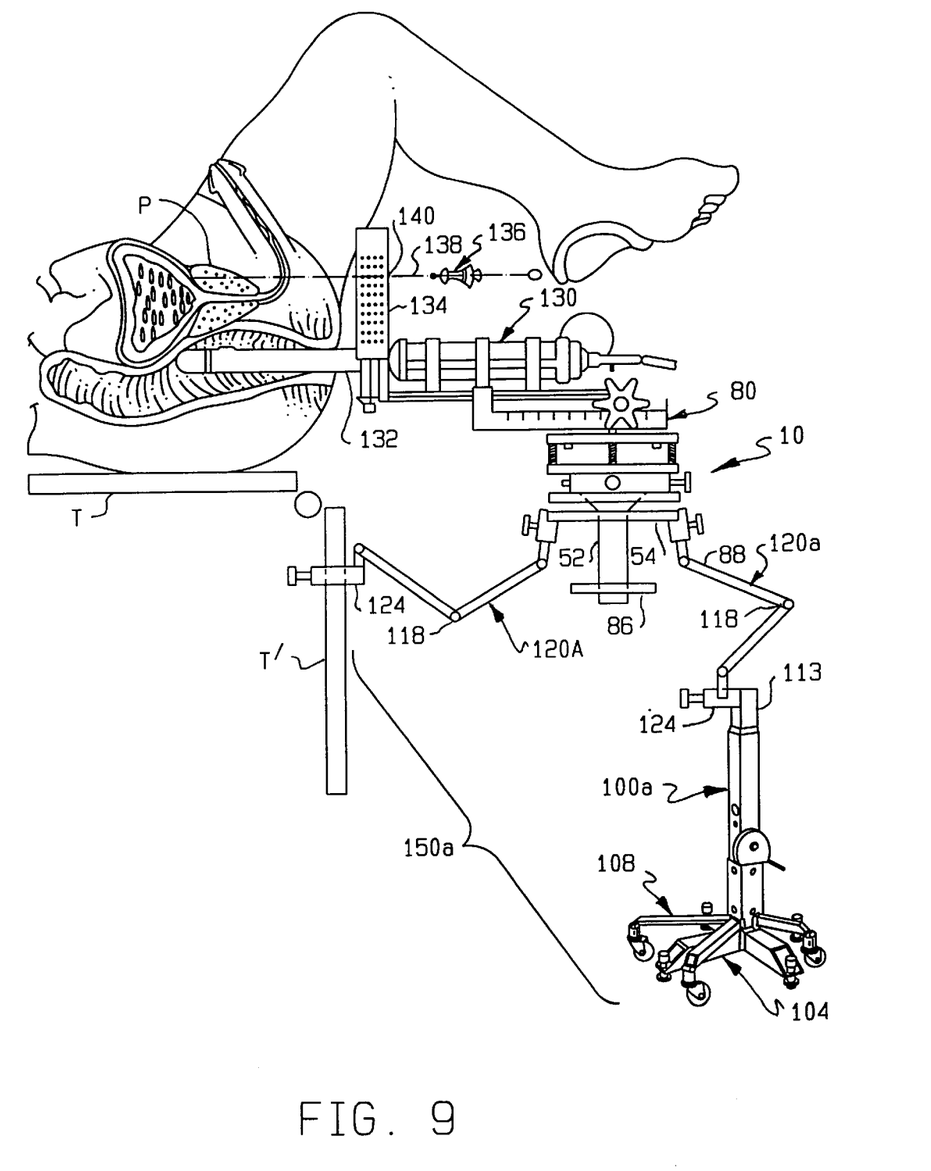
FIG. 9 is a side schematic view of the preferred embodiment of the system 150a in use.
Figure 10:
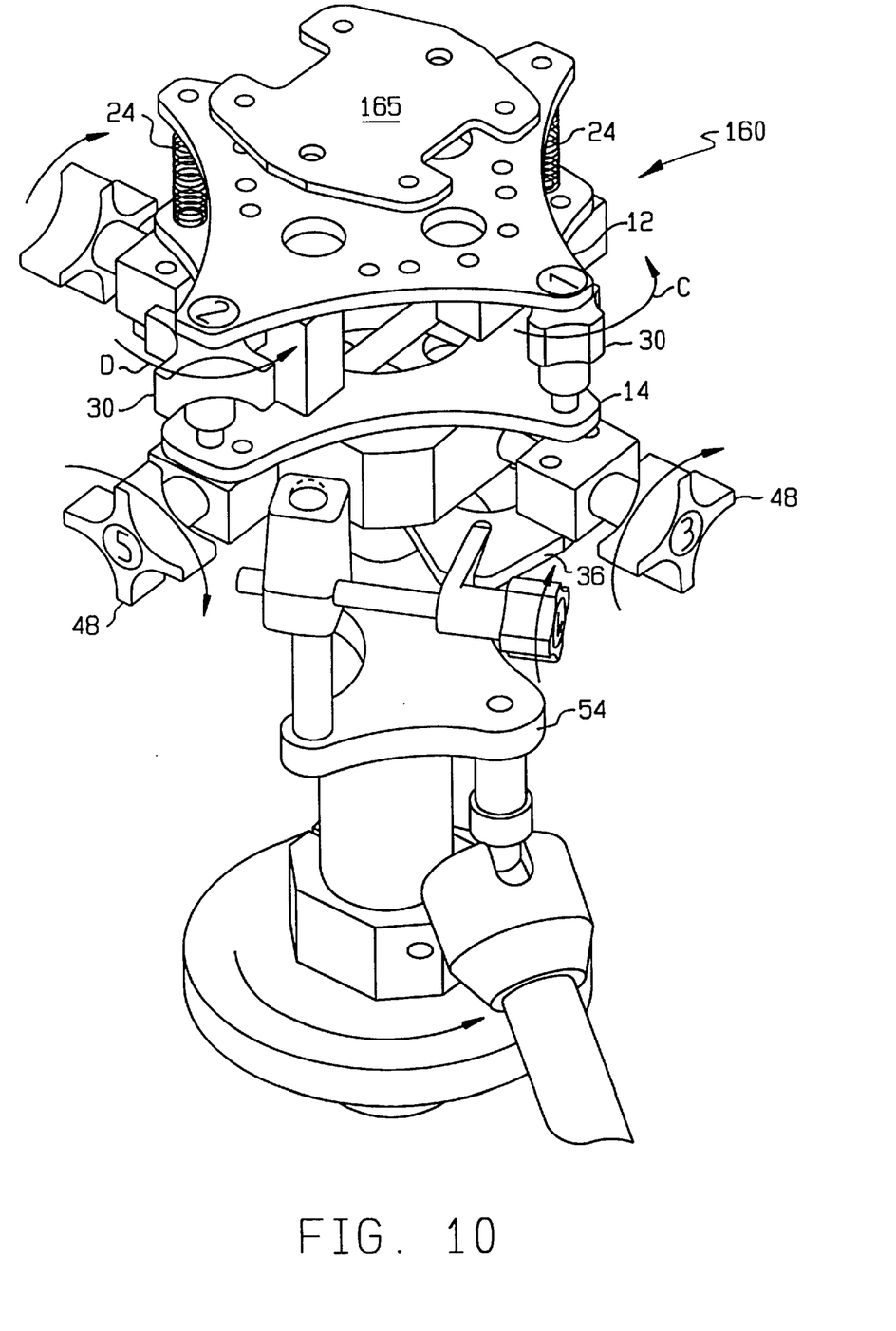
FIG. 10 is a perspective view of another preferred embodiment of another positioning apparatus according to the invention.

Referring to FIG. 9, a schematic of the preferred embodiment of the invention in use for radioactive seed implantation in a diseased prostate P of a patient is shown at numeral 150a. The omni-directional adjusting apparatus 10 has the stepping member 80 mounted thereatop. Mounted within the stepping member 80 is the transrectal ultrasound imaging probe 130 which is initially positioned manually for having probe 132 inserted into the rectal area of the patient. During the surgical procedure, one articulating arm 120a is connected to table T' while the other articulating arm 120a is connected to an upper support member 113 of floor stand 100a. Floor stand 100a is otherwise identical to the floor stand 100 previously shown and described in FIG. 7.

In one embodiment of method of use, to initially manually position the ultrasound probe 130, the locking knobs 118 of each articulating arm 120a are released. A surgeon or medical practitioner may than manually manipulate the ultrasound probe 130 by grasping shaft 52 or as may be otherwise convenient. By monitoring the image output of the ultrasound probe 130 with a conventional CRT monitor or the like, the surgeon may carefully place the probe 132 into the rectal area for optimal initial alignment. While still holding this initial alignment, locking knobs 118 of each of the articulating arm assemblies 120a are then quickly locked to secure the manually selected initial alignment and orientation of the probe 132. Should floor stand 100a be inconveniently positioned, lock member 124 may be released to remove floor stand 100a and then reconnected to another fixed or stationary object such as an edge of table T.

In a preferred method of use, only a single the articulating arm assembly 120a which is connected to table or floor stand 100a is used as above described to establish the manually selected initial placement of the ultrasound probe 130. Thereafter, the other articulating arm 120a is connected between lower plate 54 and another stationary or fixed in place object such as the edge of table T'. This preferred sequence of use minimizes obstacles that might be in the way of the surgeon performing the initial instrument placement during the procedure.

After the ultrasound image probe 130 is thus positioned and secured in the manually selected initial orientation by either of the above methods, each of the omni-directional fine adjusting mechanisms of the apparatus 10 as best shown in FIGS. 1 and 2 and as previously described may be carefully adjusted to fine tune the positioning of the probe 132. Note that each of the six adjustments for linear positioning in all three orthogonal directions and rotational orientation about all three orthogonal axes are accomplished individually and without affecting any of the other adjusted positions.

A preferred use of the system 150a is depicted in FIG. 9 in conjunction with the implantation of radioactive seeds into a diseased prostate P. This procedure is also depicted in conjunction with promotional brochures for the Martin Immobilization Device. A template 134 is connected to the stepping device 80 and generally orthogonally oriented with respect to the longitudinal axis of the ultrasound transducer 130. The transparent template 134 includes a plurality of evenly spaced small holes 140 formed therethrough to receive an implant needle 138 of a seed implant device 136. Assisted by CRT images provided by the ultrasound probe assembly 130, exact positioning of implant needle 138 and the radioactive seeds within the prostate P is achieved.

In general, the invention thus provides an instrument platform for facilitating omni-directional freehand positioning of the instrument during perineal surgery, for immediate securement of the chosen freehanded instrument positioning to at least one and preferably two fixed objects and, finally, for fine omni-directional micro-adjustment of the instrument position and angular orientation about all three linear axes and about all three axes of rotation of the platform. Perineal surgery includes surgery of the rectal, vaginal, urethral and perineal areas.

FIG. 9 shows another embodiment of the apparatus 160 of the invention. This device is essentially the same as that shown in the previous drawings, with the exception that stepping device 80 is not present. Where the same components are present as in the other figures, the same numerals have been used.

In place of stepper 80, the apparatus of FIG. 9 includes a simple support plate 165 which can be secured to plate member 12 by screws and bolts or the like. Upon this support plate 165 can be mounted any one of a wide variety of probes, biopsy guides, needles, needle guides, or other instruments for use in surgical or diagnostic procedures. One of ordinary skill in the art can easily provide the necessary adapters, supports or grips for these instruments so that they can be securely mounted to support plate 165. The apparatus 160 can then be used to enhance the accuracy and security of the procedure. For example, for percutaneous biopsy, it is easy to image the biopsy line with all necessary equipment lined up in position. This provides a positive confirmation of accuracy before and during the actual biopsy by standard imaging techniques and avoids the uncertainties and variables associated with manual manipulation.

For certain procedures, fine adjustment in only three rather than four planes provides sufficient precision. Four planes would be used for the most critical procedures for best results. Thus, the present device is useful for guided biopsy of the breasts, thyroid or kidney as well as for other intra-abdominal or retroperitoneal organs or areas. This device is designed to hold needle biopsy guides in a precise ay to allow intermittent imaging and use of a variety of odalities to confirm position before advancing the needle to biopsy the tissue of concern.

While the instant invention has been shown and described herein in what are conceived to be the most practical and preferred embodiments, it is recognized that departures may be made by one of ordinary skill in the art, and it is intended that the appended claims cover all such departures and modifications to the extent that they fall within the true spirit and scope of this invention.

What is claimed is:

1. An apparatus for use during a medical procedure comprising:
    an upper mounting plate having an upper surface adapted for mounting a medical device;
    a lockable support assembly connected to said upper mounting plate and also selectively connected to an object for allowing free omni-directional manual manipulation of a medical device into a selected initial in-use placement of the medical device with respect to a patient and for thereafter lockable securing the initial in-use placement with respect to the object without substantially altering the initial in-use placement; and wherein the lockable support assembly comprises a pair of articulating lockable arm members associate with a lower support plated; and
    an adjusting assembly positioned between said upper mounting plate and said lockable support assembly for effecting controlled omni-directional adjustment of the initial in-use placement after said lockable support assembly has been lockably secured with respect to the object.

2. An apparatus for use during a medical procedure comprising;
    a mounting plate;
    a lockable support assembly connected to said upper mounting plate and also selectively connected to an object for allowing free omni-directional manual manipulation of a medical device into a selected initial in-use placement of the medical device with respect to a patient and for thereafter lockably securing the initial in-use placement with respect to the object without substantially altering the initial in-use placement; and
    an adjusting assembly positioned between said upper mounting plate and said lockable support assembly for effecting controlled omni-directional adjustment of the initial in-use placement after said lockable support assembly has been lockably secured with respect to the object,
    wherein said apparatus further comprises a base plate and the adjusting assembly comprises a first intermediate support connected to the upper mounting plate by cross members and support blocks, where one support block is connected to the upper mounting plate, another support block is connected to the base plate, one cross-member is connected to each support block and the cross members are connected to each other to provide a pivotable connection between the upper mounting plate and the base plate.

3. The apparatus of claim 2 wherein the adjustment assembly further comprises two compression springs positioned between the upper mounting plate and the first intermediate support plate to retain the plates in spaced relation, the springs being mounted to allow separate tilting of the plates in either a first direction, a second direction oriented 90° to the first direction, or in both directions to allow the upper mounting plate to be mounted at an angular orientation to properly position the medical device.

4. The apparatus of claim 3 wherein the adjustment assembly further comprises first and second adjustment members for varying the distance between the plates, each adjustment member including means for minimizing frictional contact upon the upper mounting plate.

5. The apparatus of claim 4 wherein each adjustment member includes a body rotatably mounted upon a rod to allow movement thereupon, and a ball positioned between the body and the upper plate to minimize frictional contact therewith.

6. The apparatus of claim 2 further comprising a second intermediate support plate associated with the first intermediate support plate, and including an assembly for linearly advancing or retracting the first intermediate support plate.

7. The apparatus of claim 6 wherein the linear advancing and retracting assembly comprises an end block connected to each of the first and second intermediate plates and operatively associated with shaft members, with the blocks and shafts configured so that the plate can be advanced or retracted in either a first direction, a second direction oriented at 90° to the first direction, or in both directions.

8. An apparatus for use during a medical procedure comprising:
   an upper mounting plate;
   a lockable support assembly connected to said upper mounting plate and also selectively connected to an object for allowing free omni-directional manual manipulation of a medical device into a selected initial in-use placement of the medical device with respect to a patient and for thereafter lockably securing the initial in-use placement with respect to the object without substantially altering the initial in-use placement; and
   an adjusting assembly positioned between said upper mounting plate and said lockable support assembly for effecting controlled omni-directional adjustment of the initial in-use placement after said lockable support assembly has been lockably secured with respect to the object,
   further comprising a portable floor stand adapted for rolling movement over a floor surface, said floor stand including means for stationary positioning thereof atop a floor during positioning and use of the instrument; and
   an articulable arm member releasably connected between an upper portion of said floor stand and said adjustment assembly for allowing free omni-directional manual movement and placement of the medical device for use with respect to the patient when said articulable arm member is unlocked and for rigid immobilization of the medical device by locking said articulable arm member immediately after an initial orientation and positioning of the medical device is manually achieved, whereby the selected positioning and orientation of the medical device is substantially undisturbed and unaltered after said articulable arm member is locked.

9. The apparatus of claim 8 wherein said adjustment assembly can make finely controlled adjustments of the initial orientation and positioning of the medical device about three substantially orthogonal axes of rotation and about three substantially orthogonal linear directions after rigid immobilization of the medical device in the initial orientation and position is achieved and secured by said articulable arm member.

10. The apparatus of claim 9, further comprising a second articulable arm member releasibly connected at each end thereof between another fixed object and said medical device support and adjustment assembly for providing additional stability of the medical device during use.

11. An apparatus for supporting and securely achieving a precisely selected in-use position and angular orientation of a medical device during a medical procedure comprising:
   first, second, third and fourth spaced apart and substantially parallel and coextensive plates, said first plate adapted to supportively receive the medical device secured thereatop;
   a first adjustment assembly connected and positioned substantially between said first and second plates for making controlled angular movements between said first and second plates about rotational axes which are each substantially independent one to another and substantially parallel and laterally orthogonal to a length of the medical device;
   a second adjustment assembly connected and positioned substantially between said second and third plates for making controlled linear movements between said second and third plates which linear movements are each substantially independent one to another and substantially longitudinal and linear to the medical device; and
   a third adjustment assembly connected and positioned substantially between said third and fourth plates for making controlled vertical movements between said third and fourth plates and controlled rotation of said first and second and third plates relative to said fourth plate, which movements are substantially independent one to another; and
   a first articulable arm means releasably connected between said fourth plate and an object relative to the patient for allowing free omni-directional manual movement and placement of the medical device into an initial position and orientation with respect to a patient when said first articulable arm member is unlocked and for rigid immobilization of the medical device by locking said first articulable arm member after the initial positioning and orientation of the medical device is manually achieved whereby the initial selected positioning and orientation of the medical device is substantially undisturbed and unaltered as said first articulable arm member is locked.

12. The apparatus of claim 11, where in the a third adjustment assembly is connected between third and fourth plates for making independent, controlled rotational movements between said third and fourth plates about an upright axis and for making independent controlled linear movements between said third and fourth plates substantially along said upright axis.

13. An apparatus for supporting and securely achieving a precisely selected in-use position and angular orientation of a medical device during a medical procedure comprising:
   first, second, third and fourth spaced apart and substantially parallel and coextensive plates, said first plate adapted to supportively receive the medical device secured thereatop;
   a first adjustment assembly connected and positioned substantially between said first and second plates for making controlled annular movements between said first and second plates about rotational axes which are each substantially independent one to another and substantially parallel and laterally orthogonal to a length of the medical device;
   a second adjustment assembly connected and positioned substantially between said second and third plates for making controlled linear movements between said second and third plates which linear movements are each substantially independent one to another and substantially longitudinal and linear to the medical device; and
   a third adjustment assembly connected and positioned substantially between said third and fourth plates for making controlled vertical movements between said third and fourth plates and controlled rotation of said first, second and third plates relative to said fourth plate, which movements are substantially independent one to another; and
   a first articulable arm means releasably connected between said fourth plate and an object stationary relative to a patient for allowing free omni-directional manual movement and placement of the medical device into an initial position and orientation with respect to the patient when said first articulable arm member is unlocked and for rigid immobilization of the medical device by locking said first articulable arm member after the initial positioning and orientation of the medical device is manually achieved whereby the initial selected positioning and orientation of the medical device is substantially undisturbed and unaltered as said first articulable arm member is locked; further comprising a second articulable arm member releasably connected at each end thereof between an upper portion of a floor stand and said fourth plate for providing additional stability of the medical device during use.

14. An apparatus for supporting and securely achieving a precisely selected in-use position and angular orientation of a medical device during a medical procedure comprising:

first, second, third and fourth spaced apart and substantially parallel and coextensive plates, said first plate adapted to supportively receive the medical device secured thereatop;

a first adjustment assembly connected and positioned substantially between said first and second plates for making controlled angular movements between said first and second plates about rotational axes which are each substantially independent one to another and substantially parallel and laterally orthogonal to a length of the medical device;

a second adjustment assembly connected and positioned substantially between said second and third plates for making controlled linear movements between said second and third plates which linear movements are each substantially independent one to another and substantially longitudinal and linear to the medical device; and a third adjustment assembly connected and positioned substantially between said third and fourth plates for making controlled vertical movements between said third and fourth plates and controlled rotation of said first, second and third plates relative to said fourth plate, which movements are substantially independent one to another; and a first articulable arm means releasably connected between said fourth plate and an object stationary relative to a patient for allowing free omni-directional manual movement and placement of the medical device into an initial position and orientation with respect to the patient when said first articulable arm member is unlocked and for rigid immobilization of the medical instrument by locking said first articulable arm member after the initial positioning and orientation of the medical device is manually achieved whereby the initial selected positioning and orientation of the medical device is substantially undisturbed and unaltered as said first articulable arm member is locked; further comprising a portable floor stand adapted for rolling movement over a floor surface, said floor stand including a device for stationary positioning thereof atop a floor during positioning and use of the instrument, and said first articulable arm means being releasably connected to said floor stand.

15. A method of supporting and positioning a medical device during a medical procedure comprising:

a. providing an apparatus comprising:
  (1) a mounting plate;
  (2) a lockable support assembly connected to said mounting plate and also selectively connected to an object;
  (3) an adjusting assembly positioned between said mounting plate and said lockable support assembly; and
  (4) base plate and the adjusting assembly comprises a first intermediate support connected to the mounting plate by cross members and support blocks, where one support block is connected to the mounting plate, another support block is connected to the base plate, one cross-member is connected to each support block and the cross members are connected to each other to provide a pivotable connection between the mounting plate and the base plate;

b. connecting said lockable support assembly to an object;

c. manipulating said mounting plate into a selected initial in-use placement;

d. lockably securing said initial in-use placement with respect to the object without substantially altering the initial in-use placement; and e. selectively operating said adjusting assembly for effecting controlled omni-directional adjustment of the initial in-use placement.

16. A method of supporting and securely achieving a precisely selected in-use position and angular orientation of a medical device during a medical procedure comprising:

a. Providing an apparatus comprising:
  (1) first, second, third and fourth spaced apart and substantially parallel and coextensive plates, said first plate adapted to supportively receive the medical device secured thereatop;
  (2) a first adjustment assembly connected and positioned substantially between said first and second plates;
  (3) a second adjustment assembly connected and positioned substantially between said second and third plates;
  (4) a third adjustment assembly connected and positioned substantially between said third and fourth plates;
  (5) a first articulable arm means releasably connected between said fourth plate and an object stationary relative to a patient for allowing free omni-directional manual movement and placement of the medical device into an initial position and orientation with respect to the patient when said first articulable arm member is unlocked and for rigid immobilization of the medical device by locking said first articulable arm member after the initial positioning and orientation of the medical device is manually achieved whereby the initial selected positioning and orientation of the medical device is substantially undisturbed and unaltered as said first articulable arm member is locked;

b. connecting said first articulable arm means to a stationary object;

c. manipulating said plates into a selected initial position and orientation with respect to a patient;

d. lockably securing said initial position and orientation with respect to the stationary object without substantially altering the initial in-use placement; and e. selectively operating said first adjustment assembly for making controlled angular movements between said first and second plates about rotational axes which are each substantially independent one to another and substantially parallel and laterally orthogonal to a length of the medical device, and selectively operating said second adjustment assembly for making controlled linear movements between said second and third plates which linear movements are each substantially independent one to another and substantially longitudinal and linear to the medical device, and selectively operating said third adjustment assembly for making controlled vertical movements between third and fourth plates and controlled rotation of said first, second and third plates relative to said fourth plate which movements are substantially independent one to another.

* * * * *